(12) United States Patent
Smith

(10) Patent No.: US 6,994,087 B1
(45) Date of Patent: Feb. 7, 2006

(54) ESOPHAGEAL INTUBATION DETECTION SYSTEM

(76) Inventor: John D. Smith, 2321 Needham Dr., Valrico, FL (US) 33594

( * ) Notice: Subject to any disclaimer, the term of this patent is extended or adjusted under 35 U.S.C. 154(b) by 0 days.

(21) Appl. No.: 11/002,047

(22) Filed: Dec. 2, 2004

(51) Int. Cl.
*A61M 16/00* (2006.01)
*A61M 37/00* (2006.01)
*A62B 9/00* (2006.01)
*A62B 7/00* (2006.01)

(52) U.S. Cl. .................... 128/207.16; 128/205.13; 128/205.23; 604/142

(58) Field of Classification Search .......... 128/207.16, 128/207.14, 205.22–24, 202.28, 202.29, 128/200.26, 205.13, 203.11, 203.28, 205.23, 128/205.17, 202.22; 604/98.02, 75, 37, 991, 604/142, 99.01–99.04; 137/854, 855; 417/566
See application file for complete search history.

(56) References Cited

U.S. PATENT DOCUMENTS

| | | | | |
|---|---|---|---|---|
| 1,867,478 A | * | 7/1932 | Stelzner | ................. 137/512.15 |
| 3,070,089 A | * | 12/1962 | Dick | ..................... 128/205.12 |
| 4,226,233 A | * | 10/1980 | Kritzer | .................. 128/205.13 |
| 5,704,347 A | * | 1/1998 | Schlobohm | ............ 128/205.24 |
| 5,803,122 A | * | 9/1998 | Theilmeier | .................. 137/854 |
| 6,070,574 A | * | 6/2000 | O'Day et al. | .......... 128/203.11 |
| 6,263,875 B1 | * | 7/2001 | Pace et al. | ............. 128/207.18 |
| 6,581,598 B1 | * | 6/2003 | Foran et al. | ........... 128/204.23 |
| 6,584,974 B1 | * | 7/2003 | Ratner | .................... 128/205.23 |
| 2002/0049751 A1 | * | 4/2002 | MacRae et al. | ........ 128/200.22 |

* cited by examiner

*Primary Examiner*—Henry Bennett
*Assistant Examiner*—Andrew Bunin
(74) *Attorney, Agent, or Firm*—Edward P. Dutkiewicz

(57) ABSTRACT

An endotracheal tube bulb aspirator system has a bulb with a top end, a bottom end with an open bottom, and a transition zone therebetween. A first interior space in the top end is contiguous with a second interior space in the bottom end. At least one first flapper valve on the bulb includes at least one aperture in the bulb and an associated sheet positioned over the associated aperture with a portion of one edge being free. A second flapper valve is positioned adjacent the transitional zone between the first interior space and the second interior space has support beams and a disc with free edges coupled centrally to the support beams.

5 Claims, 4 Drawing Sheets

ESOPHAGEAL INTUBATION DETECTION SYSTEM

BACKGROUND OF THE INVENTION

1. Field of the Invention

The present invention relates to a esophageal intubation detection system and more particularly pertains to confirming the proper placement of an endotracheal tube.

2. Description of the Prior Art

The use of suction bulbs of known designs and configurations is known in the prior art. More specifically, suction bulbs of known designs and configurations previously devised and utilized for the purpose of for confirming endotracheal placement through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,591,130 to Denton discloses an esophageal intubation detector with indicator. U.S. Pat. No. 5,885,248 to Denton discloses an intubation detection system with transducer based indicator. U.S. Pat. No. 6,149,603 to Parker discloses a method and apparatus for determining whether an intubated patient has ben properly intubated. Lastly, U.S. Pat. No. 6,202,646 to Camodeca et al. discloses a detection device for verifying the proper intubation of an endotracheal tube.

While these devices fulfill their respective, particular objectives and requirements, the aforementioned patents do not describe esophageal intubation detection system that allows confirming the proper placement of an endotracheal tube.

In this respect, the esophageal intubation detection system according to the present invention substantially departs from the conventional concepts and designs of the prior art, and in doing so provides an apparatus primarily developed for the purpose of confirming the proper placement of an endotracheal tube.

Therefore, it can be appreciated that there exists a continuing need for a new and improved esophageal intubation detection system which can be used for confirming the proper placement of an endotracheal tube. In this regard, the present invention substantially fulfills this need.

SUMMARY OF THE INVENTION

In view of the foregoing disadvantages inherent in the known types of suction bulbs of known designs and configurations now present in the prior art, the present invention provides an improved esophageal intubation detection system. As such, the general purpose of the present invention, which will be described subsequently in greater detail, is to provide a new and improved esophageal intubation detection system and method which has all the advantages of the prior art and none of the disadvantages.

To attain this, the present invention essentially comprises an endotracheal tube formed of a semirigid material. The endotracheal tube is in a generally cylindrical configuration with a first diameter. The endotracheal tube has a first end and a second end. An adaptor is provided on the first end of the endotracheal tube.

Next provided is a bulb. The bulb is formed of a pliable material with a generally spherically shaped top end and a generally cylindrically shaped bottom end. A transition zone is provided between the top end and bottom end. A first interior space in the spherically shaped top end is contiguous with a second interior space in the cylindrically shaped bottom end. The cylindrically shaped bottom end has an open bottom of a second diameter being greater than the first diameter. The open bottom is adapted to receive the tube.

A plurality of primary flapper valves oriented around the transition zone of the bulb are next provided. Each primary flapper valve has a circular aperture in the bulb and an associated flapper sheet formed of a flexible material. Each flapper sheet has a generally rectangular configuration with a top edge, a bottom edge and a pair of side edges. Each flapper sheet is positioned over one of the apertures and fixed on the top edge, the side edges and a portion of the bottom edge adjacent to the side edges. In this manner, when the bulb is squeezed, air within the bulb will be compressed and forced through the apertures and past the bottom edges of the flapper sheets until the pressure inside the bulb becomes zero and the flapper sheets reseal the apertures.

Lastly, a circular flapper valve is provided. The circular flapper valve is positioned adjacent the transitional zone between the first interior space and the second interior space. The circular flapper valve has a rigid cylindrical base with a central cylindrical aperture with a third diameter. The circular flapper valve also has an internal cylinder and an external cylinder. A plurality of support beams radiate between the internal cylinder and the external cylinder. The circular flapper valve also has a pliable disc of a fourth diameter greater than the third diameter. A central securing knob is adapted to insert into the internal cylinder adjacent to the spherically shaped top end of the bulb. In this manner, when the pressure is negative within the spherically shaped top end of the bulb, air is allowed to pass from the second interior space to the first interior space; and when pressure is increased in the spherically shaped top end of the bulb by compressing the disc, air is prevented from moving from the first space into the second space and the air will look for the path of least resistance which is through the primary flapper valves. The direct connection between the adaptor of the endotracheal tube and the bulb is made possible by use of the valves whereby there is no need for the removal of the bulb each time it needs to be recompressed.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved esophageal intubation detection system which has all of the advantages of the prior art suction bulbs of known designs and configurations and none of the disadvantages.

It is another object of the present invention to provide a new and improved esophageal intubation detection system which may be easily and efficiently manufactured and marketed.

It is further object of the present invention to provide a new and improved esophageal intubation detection system which is of durable and reliable constructions.

An even further object of the present invention is to provide a new and improved esophageal intubation detection system which is susceptible of a low cost of manufacture with regard to both materials and labor, and which accordingly is then susceptible of low prices of sale to the consuming public, thereby making such esophageal intubation detection system economically available to the buying public.

Even still another object of the present invention is to provide a esophageal intubation detection system for confirming the proper placement of an endotracheal tube.

Lastly, it is an object of the present invention to provide a new and improved endotracheal tube bulb aspirator system having a bulb with a top end, a bottom end with an open bottom, and a transition zone therebetween. A first interior space in the top end is contiguous with a second interior space in the bottom end. At least one first flapper valve on the bulb includes at least one aperture in the bulb and an associated sheet positioned over the associated aperture with a portion of one edge being free. A second flapper valve is positioned adjacent the transitional zone between the first interior space and the second interior space has support beams and a disc with free edges coupled centrally to the support beams.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figures 1, 2:
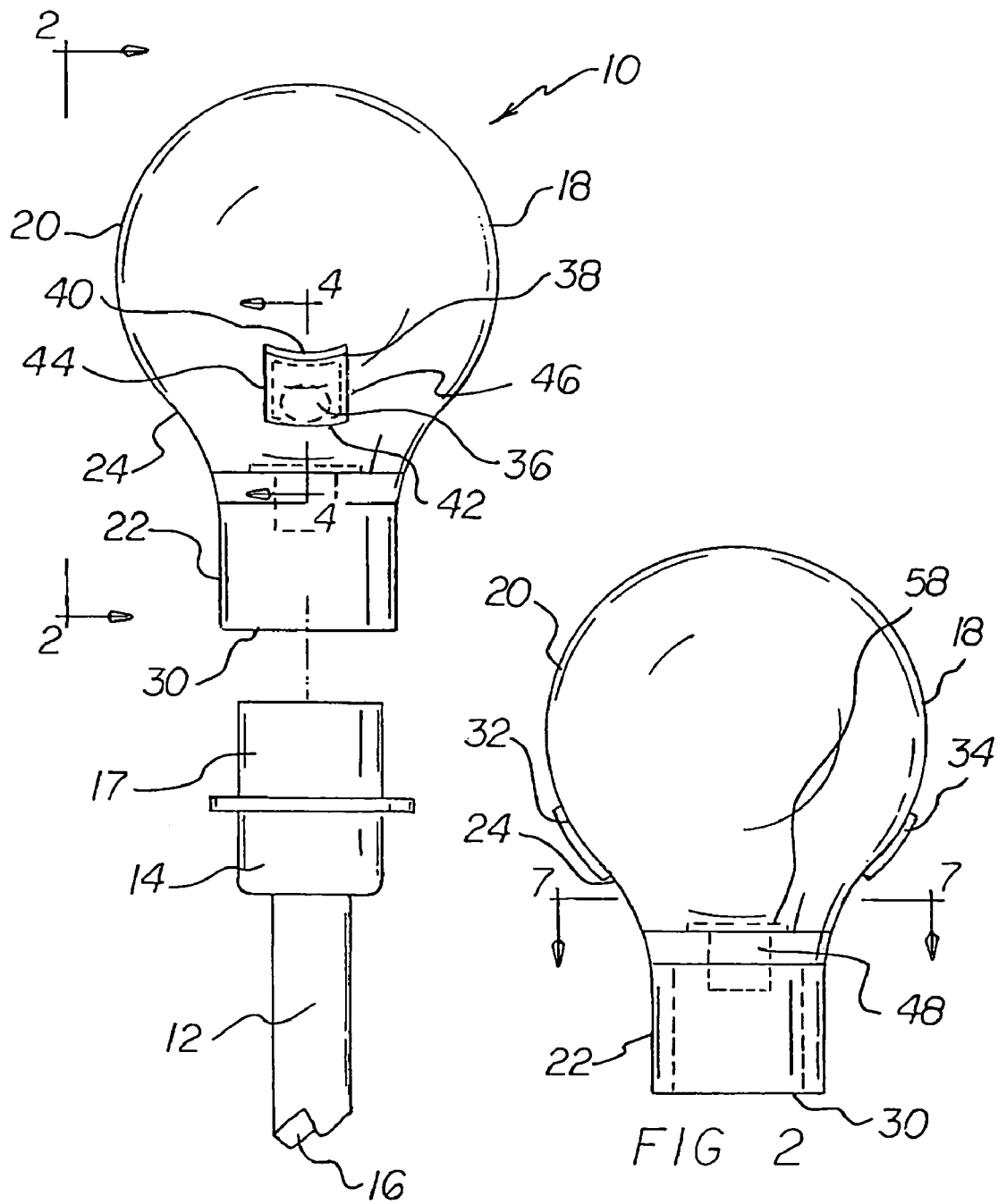
FIG. 1 is a perspective illustration of the present invention showing the bulb dislocated from the tube.
FIG. 2 is a side view of the present invention taken along line 2—2 of FIG. 1 showing the bulb.
Figure 3:
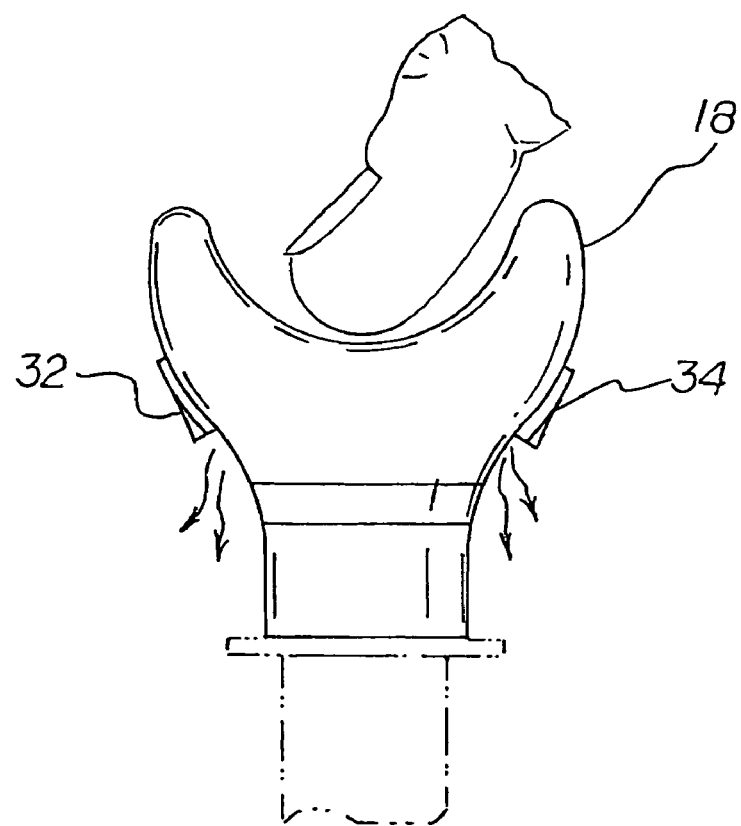
FIG. 3 is a side view of the present invention showing the system in operation when the bulb is compressed.
Figure 4:
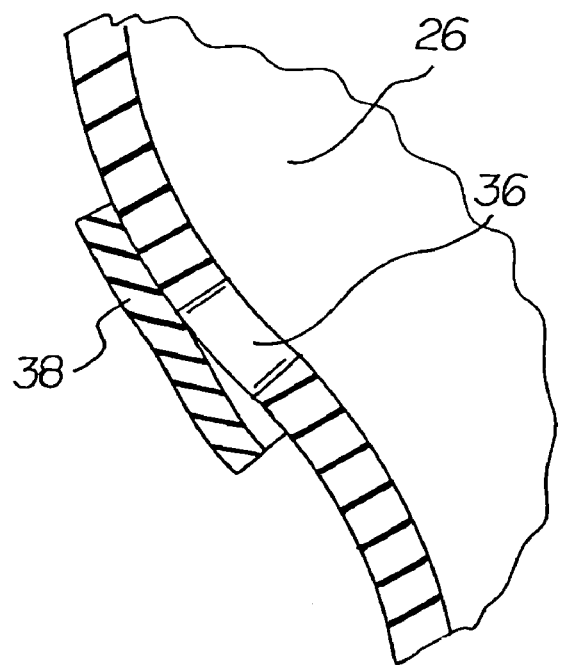
FIG. 4 is cross sectional view of rectangular flab valves taken along line 4—4 of FIG. 1 showing the attachment of the flab to the bulb.

With reference now to the drawings, and in particular to FIG. 1 thereof, the preferred embodiment of the new and improved esophageal intubation detection system embodying the principles and concepts of the present invention and generally designated by the reference numeral 10 will be described.

The present invention, the esophageal intubation detection system 10 is comprised of a plurality of components. Such components in their broadest context include a bulb, a plurality of first flapper valves, and a second flapper valve. Such components are individually configured and correlated with respect to each other so as to attain the desired objective.

First provided is an endotracheal tube 12. The endotracheal tube is formed of a semirigid material. The endotracheal tube is in a generally cylindrical configuration with a first diameter. The endotracheal tube has a first end 14 and a second end 16. An adaptor 17 is provided on the first end of the endotracheal tube.

Next provided is a bulb 18. The bulb is formed of a pliable material with a generally spherically shaped top end 20 and a generally cylindrically shaped bottom end 22. A transition zone 24 is provided between the top end and bottom end. A first interior space 26 in the spherically shaped top end is contiguous with a second interior space 28 in the cylindrically shaped bottom end. The cylindrically shaped bottom end has an open bottom 30 of a second diameter being greater than the first diameter. The open bottom is adapted to receive the tube.

A plurality of primary flapper valves 32, 34 oriented around the transition zone of the bulb are next provided. Each primary flapper valve has a circular aperture 36 in the bulb and an associated flapper sheet 38 formed of a flexible material. Each flapper sheet has a generally rectangular configuration with a top edge 40, a bottom edge 42 and a pair of side edges 44, 46. Each flapper sheet is positioned over one of the apertures and fixed on the top edge, the side edges and a portion of the bottom edge adjacent to the side edges. In this manner, when the bulb is squeezed, air within the bulb will be compressed and forced through the apertures and past the bottom edges of the flapper sheets until the pressure inside the bulb becomes zero and the flapper sheets reseal the apertures.

Lastly, a circular flapper valve 48 is provided. The circular flapper valve is positioned adjacent the transitional zone between the first interior space and the second interior space. The circular flapper valve has a rigid cylindrical base with a central cylindrical aperture 50 with a third diameter. The circular flapper valve also has an internal cylinder 52 and an external cylinder 54. A plurality of support beams 56 radiate between the internal cylinder and the external cylinder. The circular flapper valve also has a pliable disc 58 of a fourth diameter greater than the third diameter. A central securing knob 60 is adapted to insert into the internal cylinder adjacent to the spherically shaped top end of the bulb. In this manner, when the pressure is negative within the spherically shaped top end of the bulb, air is allowed to pass from the second interior space to the first interior space; and when pressure is increased in the spherically shaped top end of the bulb by compressing the disc, air is prevented from moving from the first space into the second space and the air will look for the path of least resistance which is through the primary flapper valves. The direct connection between the adaptor of the endotracheal tube and the bulb is made possible by use of the valves whereby there is no need for the removal of the bulb each time it needs to be recompressed.

Figure 5:
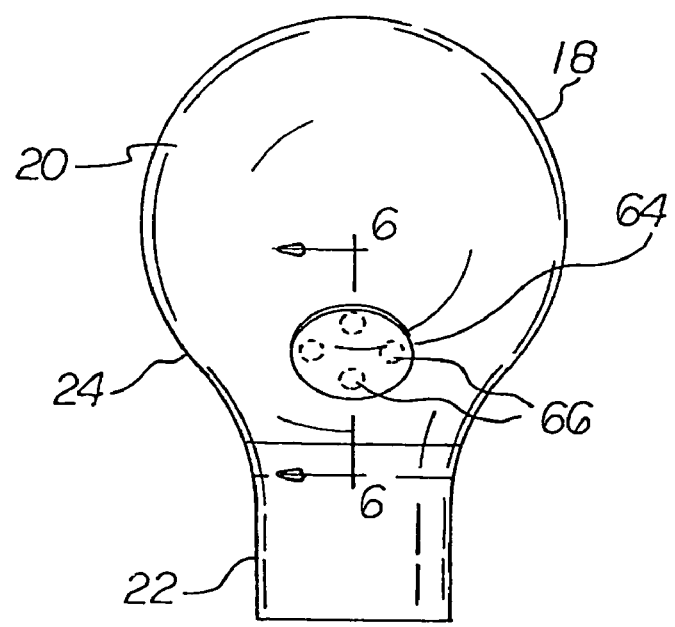
FIG. 5 is perspective view of an alternate embodiment of the present invention showing a different flap valve in the wall of the bulb.
Figure 6:
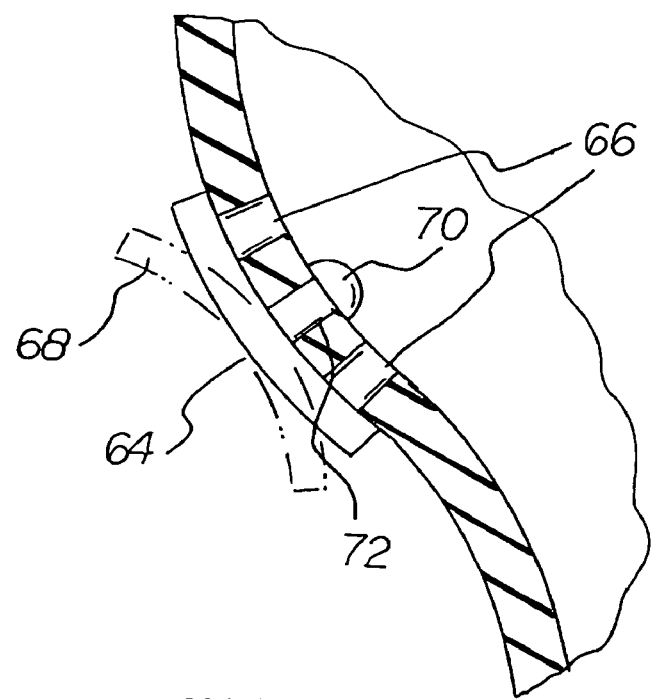
FIG. 6 is a cross sectional view of an alternate embodiment of the present invention taken along line 6—6 of FIG. 5.
Figure 7:
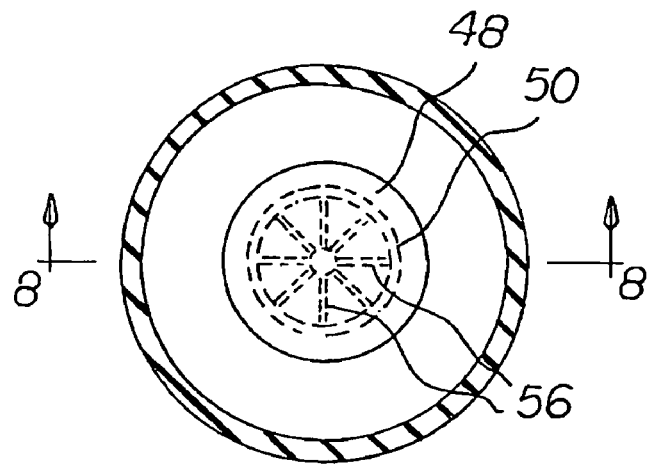
FIG. 7 is cross sectional view of the present invention taken along line 7—7 of FIG. 2 showing the cylindrical flap valve.
Figure 8:
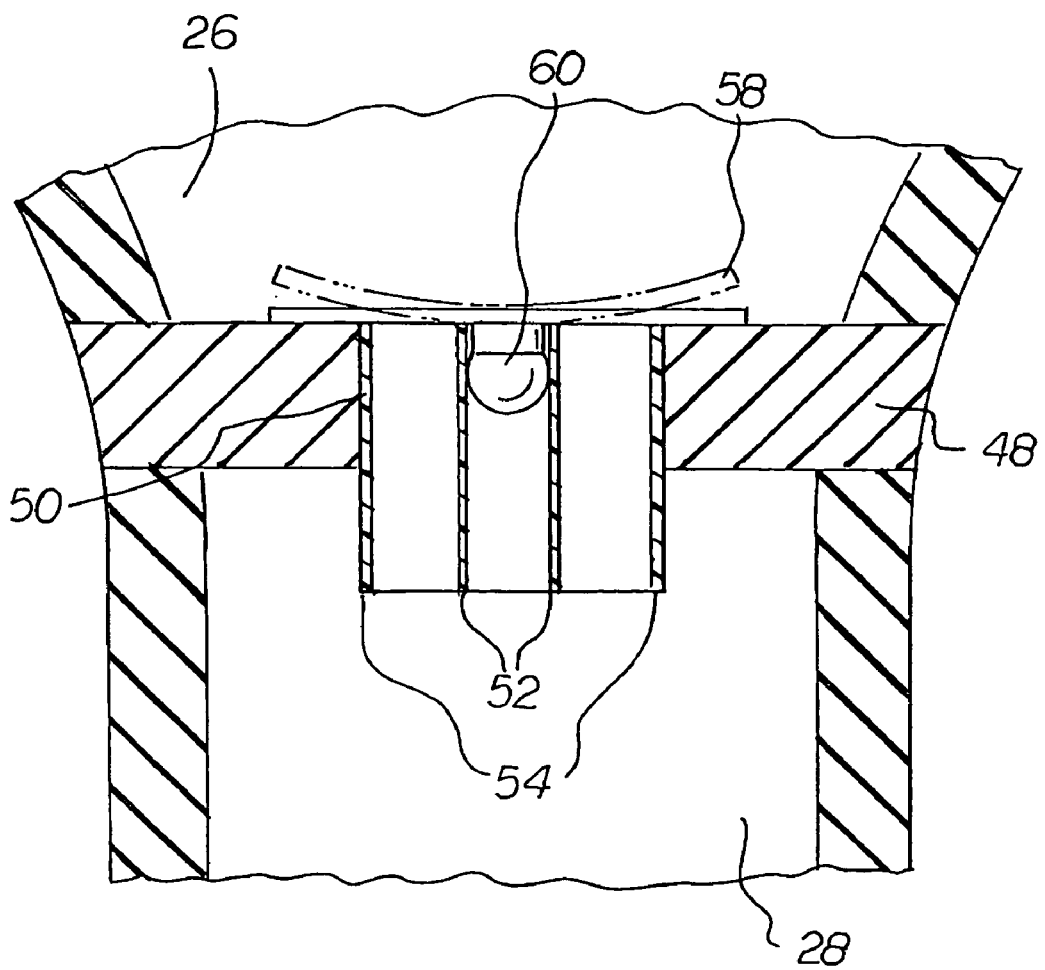
FIG. 8 is a cross sectional view of the present invention taken along line 8—8 of FIG. 7.

An alternate embodiment of the invention is shown in FIGS. 5 and 6. In such embodiment, the first flapper valve includes a disc shaped sheet 64, a plurality of circular apertures 66 in the bulb and a circular cover disc 68. In this embodiment, a knob 70 couples with a central circular aperture 72 so that the disc covers the adjacent circular apertures.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is:

1. An endotracheal tube bulb aspirator system comprising;
    a bulb having a top end, a bottom end with an open bottom, and a transition zone therebetween, a first interior space in the top end and a second continuous interior space in the bottom end;
    at least one first flapper valve on the bulb including at least one aperture in the bulb and an associated sheet positioned over the associated aperture with a portion of the sheet being free to allow the flow of air from the bulb through the at least one first flapper when the bulb is squeezed; and
    a second flapper valve positioned adjacent the transitional zone between the first interior space and the second interior space and having support beams and a disc with free edges coupled centrally to the support beams to allow the flow of air from the open bottom through the second flapper valve when the bulb is released.

2. The endotracheal tube bulb system as set forth in claim 1 wherein the at least one first flapper valve is a pair of apertures in the bulb and a pair of flexible sheets, the pair of apertures and the pair of sheets being in proximity to the transition zone on diametrical opposite sides of the bulb.

3. The endotracheal tube bulb system as set forth in claim 2 and further including an endotracheal tube with an adaptor being able to couple to the cylindrical bottom end of the bulb.

4. The endotracheal tube bulb system as set forth in claim 1 wherein the at least one of first flapper valve includes a disc shaped sheet with a plurality of circular apertures in the bulb and a circular cover disc with a knob to couple with a central circular aperture such that the disc covers the adjacent circular apertures.

5. An esophageal intubation detection system for confirming the proper placement of an endotracheal tube comprising, in combination;
    an endotracheal tube formed of a semirigid material and having a generally cylindrical configuration with a first diameter and having a first end and a second end with an adaptor on the first end of the endotracheal tube;
    a bulb formed of a pliable material with a generally spherically shaped top end and a generally cylindrically shaped bottom end with a transition zone therebetween, a first interior space in the spherically shaped top end and a contiguous second interior space in the cylindrically shaped bottom end and the cylindrically shaped bottom end with an open bottom of a second diameter being greater than the first diameter and being adapted to receive the tube;
    a plurality of primary flapper valves oriented around the transition zone of the bulb, each primary flapper valve having a circular aperture in the bulb and an associated flapper sheet formed of a flexible material, each flapper sheet having a generally rectangular configuration with a top edge, a bottom edge and a pair of side edges, each flapper sheet being positioned over one of the apertures and fixed on the top edge, the side edges and a portion of the bottom edge adjacent to the side edges, whereby when the bulb is squeezed, air within the bulb will be compressed and forced through the apertures and past the bottom edges of the flapper sheets until the pressure inside the bulb becomes zero and the flapper sheets reseal the apertures;
    a circular flapper valve positioned adjacent the transitional zone between the first interior space and the second interior space and having a rigid cylindrical base with a central cylindrical aperture with a third diameter, the circular flapper valve also having an internal cylinder, with an external cylinder, and with a plurality of support beams radiating between the internal cylinder and the external cylinder, the circular flapper valve also having a pliable disc of a fourth diameter greater than the third diameter and having a central securing knob being adapted to insert into the internal cylinder adjacent to the spherically shaped top end of the bulb such that when the pressure is negative within the spherically shaped top end of the bulb, air is allowed to pass from the second interior space to the first interior space, and whereby, when pressure is increased in the spherically shaped top end of the bulb by compressing the disc, air is prevented from moving from the first space into the second space and will look for the path of least resistance which is through the primary flapper valves, the direct connection between the adaptor of the endotracheal tube and the bulb being made possible by use of the valves and whereby there is no need for the removal of the bulb each time it needs to be recompressed.

* * * * *